United States Patent [19]

Powers et al.

[11] Patent Number: 4,845,242

[45] Date of Patent: Jul. 4, 1989

[54] ISOCOUMARINS WITH BASIC SUBSTITUENTS AS SERINE PROTEASES INHIBITORS, ANTICOAGULANTS AND ANTI-INFLAMMATORY AGENTS

[75] Inventors: James C. Powers, Atlanta; Chih-Min Kam, Roswell, both of Ga.

[73] Assignee: Georgia Tech Research Corporation, Atlanta, Ga.

[21] Appl. No.: 43,647

[22] Filed: Apr. 28, 1987

[51] Int. Cl.[4] .............................................. C07D 311/76
[52] U.S. Cl. .................................... 549/283; 549/285; 549/288; 548/336; 548/463; 548/525
[58] Field of Search ...................... 549/283, 285, 288; 548/336, 463

[56] References Cited

U.S. PATENT DOCUMENTS 2,779,762  1/1957  Robertson et al. ................. 549/285

OTHER PUBLICATIONS

Arora et al., CA 104:186277q.
Reaction of Homophthalic Acid With Phosphorus Pentachloride–V. B. Milevskaya, R. V. Belinskaya, & L. M. Yagupol'skii.
Isocourmarins: Part VI*–3-Alkoxy-4-Chloroisocoumarins, B. B. Tirookar & R. N. Usgaonkar.
Isocourmarins: Part XV–Nitro-& 7-Amino-Isocoumarins from 4– Nitrohomophthalic Acid Indira Choksey & R. N. Usgaonkar.
3-Alkoxy-7-Amino-4-chloroisocoumarins: A New Class of Suicide Substrates for Serine Protesases J. Wade Harper and James C. Powers*.
Reaction of Serine Proteases with Substituted 3-Alkoxy-4-Chloroisocoumarins and 3-Alkoxy-7-Amino-4-Chloroisocoumarins: New Reactive Mechanism-Based Inhibitors–J. W. Harper & J. C. Powers.
Reaction of Serine Proteases with Substituted Isocoumarins: Discovery of 3,4-Dichloroisocoumarin a New General Mechanism Based Serine Protease Inhibitor–J. W. Harper & J. C. Powers
New Mechanism-Based Serine Protease Inhibitors: Inhibition of Human Leukocyte Elastase, Procine Pancreatic Elastase, Human Leukocyte Cathepsin G, and Chymotrypsin by 3-Chloroisocoumarin and 3,3-Dichlorophthalide–J. W. Harper, Keiji Hemmi and J. C. Powers.
The Action of Phosphorous Pentachloride on Homophthalic Acid.

Primary Examiner—Jane T. Fan
Attorney, Agent, or Firm—Hurt, Richardson, Garner, Todd & Cadenhead

[57] ABSTRACT

Substituted isocoumarins, their preparation, their use in inhibiting serine proteases with trypsin-like, chymotrypsin-like and elastase-like specificity and their roles as anticoagulant agents, and anti-inflammatory agents.

3 Claims, No Drawings

ISOCOUMARINS WITH BASIC SUBSTITUENTS AS SERINE PROTEASES INHIBITORS, ANTICOAGULANTS AND ANTI-INFLAMMATORY AGENTS

STATEMENT OF GOVERNMENT INTEREST

This invention was made with government support under Contract No. HL34035 awarded by the National Institutes of Health, National Heart, Lung and Blood Institute. The government has certain rights in the invention.

BACKGROUND OF THE INVENTION

1. Field of the Invention

This invention relates to a novel class of heterocyclic compounds useful for selectively inhibiting trypsin-like enzymes, selectively inhibiting chymotrypsin-like enzymes, selectively inhibiting elastase or for generally inhibiting serine proteases of all classes. This invention also relates to a method of controlling blood coagulation, tumor invasiveness and treating inflammation in patients using the novel compounds of the present invention. We have found that substituted isocoumarins are potent inhibitors of blood coagulation enzymes, complement enzymes, tryptases, kallikreins, plasmin and elastase, therefore they are useful as anticoagulants, anti-inflammatory and anti-tumor agents.

2. Description of the Related Art

Serine proteases play critical roles in several physiological processes such as digestion, blood coagulation, complement activation, fibrinolysis, and reproduction. Serine proteases are not only a physiological necessity, but also a potential hazard if they are not controlled. Blood coagulation serine proteases are responsible for vascular clotting, cerebral infarction, and cornary infarction. Plasmin is involved in tumor invasiveness, tissue remodeling, and clot dissociation. Uncontrolled proteolysis by other serine proteases such as elastases may cause pancreatitis, emphysema, rheumatoid arthritis, inflammation and adult respiratory distress syndrome. Accordingly, specific and selective inhibitors of these proteases should be potent anticoagulants, anti-inflammatory agents and anti-tumor agents useful in the treatment of protease-releated diseases (Powers and Harper, in Proteinase Inhibitors, Barrett and Salvesen, eds., Elsevier, 1986, pp 55-152, incorporated herein by reference). In vitro proteolysis by trypsin, chymotrypsin or the elastase family is a serious problem in the production, purification, isolation, transport or storage of peptides and proteins.

SUMMARY OF THE INVENTION

It is an object of this invention to find a novel group of specific inhibitors for trypsin, elastase, chymotrypsin and other serine proteases of similar substrate specificity and for serine proteases in general. Inhibitors are compounds that reduce or eliminate the catalytic activity of the enzyme. Trypsin and trypsin-like enzymes normally cleave peptide bonds in proteins and peptides where the amino acid residue on the carbonyl side of the split bond ($P_1$ residue) is Lys or Arg. Elastase and elastase-like enzymes, on the other hand, cleave peptide bonds where the $P_1$ amino acid is Ala, Val, Ser, Leu and other similar amino acids. Chymotrypsin and chymotrypsin-like enzymes hydrolyze peptide bonds where $P_1$ amino acid is Trp, Tyr, Phe, Met, Leu or other amino acid residues which contain aromatic or large alkyl side chains. All of the above enzymes have extensive secondary specificity and recognize amino acid residues removed from the $P_1$ residue.

It is an object of this invention to discover new protease inhibitors, especially blood coagulation enzyme inhibitors, complement enzyme inhibitors, tryptase inhibitors, elastase inhibitors, and plasmin inhibitors. These inhibitors are useful for controlling blood coagulation, various inflammatory conditions, and tumor invasiveness mediated by serine proteases. The inhibitors of this invention would be useful for treating diseases related to blood coagulation enzymes, complement proteins or plasmin; such as vascular clotting, cerebral infarction, coronary infarction, inflammation and tumor invasiveness. The inhibitors of this invention would also be useful for treating diseases such as pancreatitis, emphysema or infantile and adult respiratory distress syndrome, which involve the destruction of tissue by serine proteases. The inhibitors of this invention would also be useful for controlling hormone processing by serine proteases and for treating diseases related to tryptases such as inflammation and skin blistering.

It is another object of this invention to find a novel group of specific inhibitors useful in vitro for inhibiting trypsin, elastase, chymotrypsin and other serine proteases of similar specificity and for inhibiting serine proteases in general. Such inhibitors could be used to identify new proteolytic enzymes encountered in research. They could also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts or other proteins and peptides which are widely sold for use in clinical analyses, biomedical research, and for many other reasons. For some uses a specific inhibitor would be desirable, while in other cases, an inhibitor with general specificity would be preferred.

DETAILED DESCRIPTION OF THE INVENTION

Substituted isocoumarins have been found to be excellent inhibitors of several serine proteases including bovine thrombin, bovine factor Xa, human factor Xa, human factor XIa, human factor XIIa, human plasma kallikrein, porcine pancreatic kallikrein, bovine trypsin, human plasma plasmin, sheep lung lymph tryptase, human complement proteins D, B, C2, human leukocyte elastase, porcine pancreatic elastase, bovine chymotrypsin and human leukocyte cathepsin G. These compounds inhibit the serine proteases by the reaction with the active site serine to form an acyl enzyme, which in some cases may further react with another active site nucleophile to form an additional covalent bond. These structures may be used in vivo to treat diseases resulting from abnormal or uncontrolled blood coagulation or diseases caused by uncontrolled proteolysis by elastase, chymotrypsin, trypsin and related serine proteases. These inhibitors may be used in vitro to prevent proteolysis which occurs in the process of production, isolation, purification, storage or transport of peptides and proteins. The novel substituted isocoumarin and related heterocyclic compounds have the following structural formula:

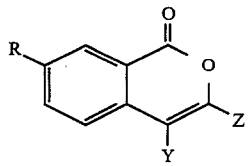

or a pharmaceutically acceptable salt, wherein

R is selected from the group consisting of —NH—C(=NH)—NH$_2$, —C(=NH)NH$_2$, C$_{1-6}$ alkyl with an attached amino, and C$_{1-6}$ alkyl with an attached isothiureido of the formula —S—C(=NH$_2{}^+$)NH$_2$, Z is selected from the group consisting of H, halogen, C$_{1-6}$ alkyl, C$_{1-6}$ alkyl with an attached phenyl, C$_{1-6}$ fluorinated alkyl, C$_{1-6}$ alkyl with an attached hydroxyl, C$_{1-6}$ alkyl with an attached C$_{1-6}$ alkoxy, C$_{1-6}$ alkoxy, C$_{1-6}$ fluorinated alkoxy, C$_{1-6}$ alkoxy with an attached phenyl, benzyloxy, 4-fluorobenzyloxy, —OCH$_2$C$_6$H$_4$R' (2-substituent), —OCH$_2$C$_6$H$_4$R' (3-substituent), —OCH$_2$C$_6$H$_4$R' (4-substituent), —OCH$_2$C$_6$H$_3$R$_2$' (2,3-substituents), —OCH$_2$C$_6$H$_3$R$_2$' (2,4-substituents), —OCH$_2$C$_6$H$_3$R$_2$' (2,5-substituents), —OCH$_2$C$_6$H$_3$R$_2$' (2,6-substituents), —OCH$_2$C$_6$H$_3$R$_2$' (3,4-substituents), and OCH$_2$C$_6$H$_3$R$_2$' (3,5-substituents), R' is selected from the group consisting of H, halogen, trifluoromethyl, NO$_2$, cyano, methyl, methoxy, acetyl, carboxyl, OH, and amino, Y is selected from the group consisting of H, halogen, trifluoromethyl, methyl, OH, and methoxy.

Alternately the novel isocoumarin and related heterocyclic compounds are represented by structure (I) where, Z is selected from the group consisting of C$_{1-6}$ alkoxy with an attached amino, C$_{1-6}$ alkoxy with an attached isothiureido, C$_{1-6}$ alkoxy with an attached guanidino, C$_{1-6}$ alkoxy with an attached amidino, C$_{1-6}$ alkyl with an attached amino, C$_{1-6}$ alkyl with an attached isothiureido, C$_{1-6}$ alkyl with an attached guanidino, C$_{1-6}$ alkyl with an attached amidino, R is selected from the group consisting of H, OH, NH$_2$, NO$_2$ halogen, C$_{1-6}$ alkoxy, C$_{1-6}$ fluorinated alkoxy, C$_{1-6}$ alkyl, C$_{1-6}$ alkyl with an attached amino, M—AA—NH—, M—AA—O—, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, alpha-aminobutyric and epsilon-aminocaponic acid, citrulline, hydroxyproline, ornithine and sarcosine, wherein M represents H, lower alkanoyl having 1 to 6 carbons, carboxyalkanoyl, hydroxyalkanoyl, amino-alkanoyl, benzene sulfonyl, tosyl, benzoyl, and lower alkyl sulfonyl having 1 to 6 carbons, Y is selected from the group consisting of H, halogen, trifluoromethyl, methyl, OH and methoxy.

Alternately the novel isocoumarin and related heterocyclic compounds are represented by structure (I) where, R is selected from the group consisting of —NH—C(=NH)—NH$_2$, —C(=NH)NH$_2$, C$_{1-6}$ alkyl with an attached amino, C$_{1-6}$ alkyl with an attached isothiureido, Z is selected from the group consisting of C$_{1-6}$ alkoxy with an attached amino, C$_{1-6}$ alkoxy with an attached isothiureido, C$_{1-6}$ alkoxy with an attached guanidino, C$_{1-6}$ alkoxy with an attached amidino, C$_{1-6}$ alkyl with an attached amino, C$_{1-6}$ alkyl with an attached isothiureido, C$_{1-6}$ alkyl with an attached guanidino, C$_{1-6}$ alkyl with an attached amidino, Y is selected from the group consisting of H, halogen, trifluoromethyl, methyl, OH and methoxy.

Other substituted isocoumarins have been prepared earlier for other purposes (illustrative examples: Davies and Poole, J. Chem. Soc., pp 1616–1629 (1928); Milevskaya, Belinskaya, and Yagupol'skii, Zhur. Org. Khim. 9, pp 2145–2149 (1973); Tirodkar and Usgaonkar, Ind. J. Chem. 7, pp 1114–1116 (1969); Choksey and Usgaonkar, Ing. J. Chem. 14B, pp 596–598 (1976), the preceding articles are incorporated herein by reference).

A number of other substituted isocoumarins have been prepared recently for inhibition of serine proteases (Harper, Hemmi, and Powers, J. Am. Chem. Soc. 105, pp 6518–6520 (1983); Harper, Hemmi, and Powers, Biochemistry 24, pp 1831–1841 (1985); Harper and Powers, J. Am. Chem. Soc. 106, pp 7618–7619 (1984); Harper and Powers, Biochemistry 24, 7200–7213 (1983), the preceding articles are incorporated herein by reference; and Powers and Harper, U.S. Pat. No. 4,596,822, which is also incorporated by reference).

The following compounds are representative of the invention:

3-(3-aminopropoxy)isocoumarin
3-(3-aminopropoxy)-4-chloroisocoumarin
3-(2-isothiureidoethoxy)-4-chloroisocoumarin
3-(3-isothiureidopropoxy)-4-chloroisocoumarin
7-amino-3-(3-isothiureidopropoxy)-4-chloroisocoumarin
7-guanidino-3-methoxyisocoumarin
7-guanidino-3-methoxy-4-chloroisocoumarin
7-guanidino-3-ethoxyisocoumarin
7-guanidino-3-ethoxy-4-chloroisocoumarin
7-guanidino-3-(2-phenylethoxy)isocoumarin
7-guanidino-3-(2-phenylethoxy)-4-chloroisocoumarin.

It has been found that compounds of Formula (I) have anticoagulant activity as shown in Table I and Table VI by effective inhibitions of the proteolytic function of blood coagulation enzymes in Hepes buffer and in human plasma. It has also been found that compounds of formula (I) have anti-tumor activity as shown in Table I by the effective inhibition of the proteolytic function of human plasma plasmin. Compounds of Formula (I) are effective in the treatment of organic rejection as shown in Table II by the effective inhibition of the proteolytic function of complement proteins. Compounds of Formula (I) have anti-inflammatory activity and are effective in the prevention and inhibition of edema and granuloma tissue formation as shown in Table IV by the effective inhibition of the proteolytic function of human leukocyte elastase. Compounds of Formula (I) are effective in the detection, prevention and inhibition of adult and infantile respiratory distress syndrome (a consequence of acute lung injuries) as shown in Table III by the effective inhibition of the proteolytic function of sheep lung lymph tryptase. Sheep lung lymph tryptase is utilized as a marker of lung capillary injury, and this is shown in the article by Lesser et al., Am. Rev. Respir. Dis. 135, pp 643-650 (1987), which is incorporated herein by reference.

Inactivation rates of serine proteases by substituted isocoumarins were measured by incubation method. An aliquot of inhibitor (25 or 50 μl) in Me$_2$SO was added to a buffered enzyme solution (0.01-2.3 μM) to initiate the inactivation. Aliquots (50 μl) were withdrawn at various intervals and the residual enzymatic activity was measured. Me$_2$SO concentration in the reaction mixture was 8-12% (v/v). 0.1 Hepes, 0.01M CaCl$_2$, pH 7.5 buffer was utilized for trypsin and coagulation enzymes. 0.1M Hepes, 0.5M NaCl, pH 7.5 was utilized for other serine proteases. The inhibitor concentrations are shown in the Tables I, II, III, and IV. Peptide thioesters or peptide nitroanilides with appropriate sequence were used as substrates for various serine proteases. All peptide thioester hydrolysis rates were measured with assay mixtures containing 4,4'-dithiodipyridine ($\epsilon_{324}$=19,800M$^{-1}$cm$^{-1}$; Grasetti & Murray, Arch. Biochem. Biophys. 119, pp 41-49 (1967)). Peptide 4-nitroanilide hydrolysis was measured at 410 nm ($\epsilon_{410}$=8800M$^{-1}$cm$^{-1}$; Erlanger et al., Arch. Biochem. Biophys. 95, pp 271-278 (1961)). First order inactivation rate constant ($k_{obs}$) were obtained from plots of In vt/V$_o$ vs time, and the correlation coefficients were greater than 0.98.

Table I shows the inactivation rate constants for several trypsin-like serine proteases inhibited by substituted isocoumarins. When the isocoumarin structure contains basic functional groups such as guanidino as R, or aminoalkoxy, isothiureidoalkoxy as Z, and Cl as Y, the compound is generally a good inhibitor for trypsin and blood coagulation enzymes and tryptases. The inactivation of the enzyme is time dependent, and the $k_{obs}/[I]$ values are second order rate constants. In most cases, inactivation of the enzyme occurs at the inhibitor concentration of 5-400 times the enzyme concentration and the first order rate constant $k_{obs}$ is obtained. However, in some cases, the inactivation was too fast to be measured under first order rate conditions ($[I]>[E]$), the inactivation rate was measured either in the presence of substrate using the progress curve method as described by Tian and Tsou, Biochemistry 21, pp 1028-1032 (1982) or using the same concentration of enzyme and inhibitor. 7-guanidino-4-chloro-3-alkoxyisocoumarins are essentially stoichiometric inactivators of trypsin, thrombin and kallikrein. The inactivation rate of the enzyme depends on the substituents R, Z and Y. The structure with R groups of guanidino, and Y groups of Cl is the best inhibitor for trypsin and all the coagulation enzymes tested. The isocoumarins with Y groups of Cl and Z groups of isothiureidoalkoxy are potent inhibitors toward trypsin-like enzymes. 7-Guanidino-3-methoxy-4-chloroisocoumarin is a good inhibitor for plasmin.

Table II shows the inactivation of complement proteins D, B, C$_2$ by substituted isocoumarins. 3-Isothiureidoalkoxy-4-chloroisocoumarins inhibit protein B and C$_2$, while other serine protease inhibitors such as 4-amidinophenylmethane sulfonyl fluoride (APMSF) and 3,4-dichloroisocoumarin do not show any inhibition toward these two enzymes. Table III shows the inactivation of sheep lung lymph tryptase by substituted isocoumarins. 7-Guanidino-3-alkoxy-4-chloroisocoumarins are good inhibitors for the tryptase. Table IV shows the inactivation rate constant for porcine pancreatic elastase (PPE), human leukocyte elastase (HLE), chymotrypsin and cathepsin G inhibited by substituted isocoumarins. Although the inactivation by the inhibitors was less efficient toward these four enzymes than trypsin-like enzymes, the isocoumarin with R group of guanidino, Y group of Cl, and Z-group of ethoxy is a good inhibitor for PPE, HLE and cathepsin G. The structure with Z-group of 2-phenylethoxy is best at inhibiting chymotrypsin.

The spontaneous hydrolysis rates of these substituted isocoumarins in Hepes buffer solution and plasma have been measured and summarized in Table V. The isocoumarins with H at position 4 are 3-6 times more stable than the compounds with Cl at the same position. 7-Amino-4-chloro-3-(3-isothiureidopropoxy)isocoumarin is fairly stable in plasma. 7-Guanidino-4-chloro-3-alkoxyisocoumarins are hydrolyzed in plasma with half-lives of 5-8 min.

Table VI shows the prothrombin time of human plasma measured in the presence of various inhibitors. 7-Guanidino-3-methoxy-4-chloroisocoumarin and 7-guanidino-3-ethoxy-4-chloroisocoumarin can prolong the slotting time from 11-14 sec to 168, and >240 sec respectively without preincubation of plasma and inhibitor. With preincubation, these two compounds still can prolong the time to 23 and 80 sec respectively.

Anticoagulants can prolong the clotting time of human plasma and play important roles in the treatment of blood coagulation related diseases such as vascular clotting, cerebral infarction and coronary infarction (Williams et al., Hemotalogy, 3rd ed. McGraw Hill, 1983 and Ingram et al., Bleeding Disorders, 2nd ed. Blackwell Scientific Publications, 1985. These two books are incorporated herein by reference). The presence of certain inhibitors of this invention in the human plasma would prolong the prothrombin time quite effectively, thus these inhibitors would act as anticoagulants in vivo. Currently, there are a few anticoagulant drugs in use clinically, and the inhibitors described in this invention can be used as anticoagulants in the treatment of animals.

It is known that in vitro activity of elastase inhibitors correlates with in vivo activity in animal models of emphysema and inflammation (Otterness et al., editor, Advances in Inflammation Research, Vol. 11, Raven Press 1986, and this article is incorporated herein by reference). Thus the novel inhibitors described here should be useful for the treatment of emphysema and inflammation. Elastase inhibitors have been used orally, by injection or by instillation in the lungs in animal studies (Powers, Am. Rev. Respir. Dis., 127, s54-s58 (1983); Powers and Bengali, Am. Rev. Respir. Dis. 134, pp 1097-1100 (1986) and these two articles are incorporated herein by reference). The inhibitors described above can be used by any of these routes.

For treatment of blood coagulation-related diseases, tumor invasiveness or inflammation, the compounds of Formula (I) may be administered orally, topically or parenterally. The term parenteral as used includes subcutaneous injection, intravenous, intramuscular, intrasternal injection or infusion techniques. The pharmaceutical compositions containing the active ingredient may be in a form suitable for oral use, for example as tablets, troches, lozenges, aqueous or oily suspensions, dispersible powders or grannules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

To use the above inhibitors in vitro, they are dissolved in an organic solvent such as dimethylsulfoxide or ethanol, and are added to an aqueous solution containing serine proteases. The final concentration of the organic solvent should be less than 25%. The inhibitors may also be added as solids or in suspension. The serine protease inhibitors of this invention would be useful in a variety of experimental procedures where proteolysis is a significant problem. Inclusion of these inhibitors in a radioimmunoassay experiments would result in higher sensitivity. The use of these inhibitors in plasma fractionation procedures would result in higher yields of valuable plasma proteins and would make purification of the proteins easier. The inhibitors disclosed here would be used in cloning experiments utilizing bacterial cultures, yeast and purified cloned product in higher yield.

TABLE I

Inactivation Rates for Inhibition of Trypsin-Like Serine Proteases by Substituted Isocoumarins

| Inhibitors | $k_{obs}/[I]$ $(M^{-1}s^{-1})$ | | | | | | | | |
|---|---|---|---|---|---|---|---|---|---|
| | bovine thrombin[b] | bovine factor Xa[c] | human factor Xa[d] | porcine pancreatic kallikrein[e] | human plasma kallikrein[f] | human factor XIa[g] | human factor XIIa[h] | bovine trypsin[i] | human plasma plasmin[j] |
| 3-(3-aminopropoxy)-isocoumarin | 3.0 | NI[k] | | 5.0 | 30 | 30 | 3.0 | 1,200 | 36 |
| 3-(3-aminopropoxy)-4-chloroisocoumarin | 350 | 160 | | 860 | 1,400 | 380 | 190 | 7,600 | 770 |
| 3-(2-isothiureidoethoxy)-4-chloroisocoumarin | 4,700 | 5,600 | | 12,000 | 280,000[l] | 44,000 | 39,000 | 32,000 | |
| 3-(3-isothiureidopropxy)-4-chloroisocoumarin | 1,430 | 220 | | 19,000 | >110,000[l] | 47,000 | 27,000 | 46,000 | |
| 7-amino-3-(3-isothiureidopropoxy)-4-chloroisocoumarin | 630 | 1,640 | 60 | >110,000[m] | 1,100 | 22,000 | 6,200 | 410,000[n] | |
| 7-guanidino-3-methoxy-isocoumarin | 4,900 | 460 | | 1,900 | 13,000 | 1,400 | 520 | 3,300 | 320 |
| 7-guanidino-3-methoxy-4-chloroisocoumarin | 290,000[n] | 3,100 | 11,000 | 45,000[n] | 240,000[n] | 36,200 | 20,000 | 310,000[n] | 3,500 |
| 7-guanidino-3-ethoxy-isocoumarin | 3,700 | 2,700 | | 16,000 | 44,000 | 3,100 | 1,300 | 20,000 | |
| 7-guanidino-3-ethoxy-isocoumarin | >55,000[m] | 26,700 | 11,000 | >200,000[m] | >500,000[l] | 60,000 | 22,000 | >110,000[m] | |
| 7-guanidino-3-(2-phenylethoxy)isocoumarin | 5,700 | 11,000 | | 16,000 | 62,000 | 1,200 | 690 | 45,000 | |
| 7-guanidino-3-(2-phenylethoxy)-4-chloro-isocoumarin | >30,000[m] | 96,000 | 11,000 | 200,000[m] | >270,000[l] | 20,000 | 26,000 | >110,000[m] | |

[a]Conditions were as 0.1 M Hepes, 0.01 M CaCl$_2$, pH 7.5 and 8–12% Me$_2$SO and 25° C. Rate constants were measured by incubation method unless otherwise noted. An aliquot of inhibitor was added to an enzyme solution and aliquots removed with time and assayed for remaining enzymatic activity. First-order rate constants, k$_{obs}$ were obtained from the plots of ln (v$_t$/v$_o$) versus time.
[b]Inhibitor concentrations were from 0.3 to 400 μM.
[c]Inhibitor concentrations were from 0.4 to 310 μM.
[d]Inhibitor concentrations were from 5 to 105 μM.
[e]Inhibitor concentrations were from 0.4 to 300 μM.
[f]Inhibitor concentrations were from 0.3 to 300 μM.
[g]Inhibitor concentrations were from 3 to 330 μM.
[h]Inhibitor concentrations were from 3 to 330 μM.
[i]Inhibitor concentrations were from 1 to 12 μM.
[j]Inhibitor concentrations were from 8 to 330 μM.
[k]No inhibition.
[l]Inactivation was extremely rapid, and the k$_{obs}$/[I] values were based on the residual enzymatic acitivty at 0.2 min.
[m]Second-order rate constant was obtained from same concentration of enzyme and inhibitor.
[n]Inactivation rate constants were obtained by progress curve method described by Tran and Tsou, Biochemistry 21, 1028–1032 (1982).

TABLE II

Inactivation of Complement Proteins by Substituted Isocoumarins and APMSF[a]

| Inhibitors | $k_{obs}/[I]$ $(M^{-1}s^{-1})$ | | |
|---|---|---|---|
| | D[b] | C$_2$[c] | B[c] |
| APMSF | 110 | NI[d] | NI |
| 3,4-dichloroisocoumarin | 192 | NI[11] | NI |
| 3-(2-isothiureidoethoxy)-4-chloroisocoumarin | 61 | 1.5 | 13 |
| 3-(3-isothiureidopropoxy)-4-chloroisocoumarin | 145 | 0.5 | 0.4 |

[a]Conditions were 0.1 M Hepes, 0.5 M NaCl, pH 7.8, 8–10% Me$_2$SO and at 25° C. The inactivation rates were measured by incubation method.
[b]Inhibitor concentration were from 0.5 to 0.12 mM.
[c]Inhibitor concentration were from 0.3 to 1.25 mM.
[d]No inhibition.

TABLE III

The Inactivation Rates of Sheep Lung Lymph Tryptase by Substituted Isocoumarins and APMSF[a]

| Inhibitors | [I](mM) | $k_{obs}/[I](M^{-1}s^{-1})$ |
|---|---|---|
| 3,4-dichloroisocoumarin | 0.46 | 39 |
| 3-(3-aminopropoxy)isocoumarin | 0.31 | 8.1 |
| 3-(3-aminopropoxy)-4-chloroisocoumarin | 0.26 | 18 |
| 3-(2-isothiureidoethoxy)-4-chloro-isocoumarin | 0.028 | 290 |
| 3-(3-isothiureidopropoxy)-4-chloro-isocoumarin | 0.036 | 230 |
| 7-amino-3-(3-isothiureidopropoxy)- | 0.038 | 710 |

TABLE III-continued

The Inactivation Rates of Sheep Lung Lymph Tryptase by Substituted Isocoumarins and APMSF[a]

| Inhibitors | [I](mM) | $k_{obs}/[I](M^{-1}s^{-1})$ |
|---|---|---|
| 4-chloroisocoumarin | | |
| 7-guanidino-3-methoxyisocoumarin | 0.043 | 53 |
| 7-guanidino-3-methoxy-4-chloroisocoumarin | 0.012 | 620 |
| 7-guanidino-3-ethoxyisocoumarin | 0.042 | 150 |
| 7-guanidino-3-ethoxy-4-chloroisocoumarin | 0.011 | 2200 |
| 7-guanidino-3-(2-phenylethoxy)isocoumarin | 0.049. | 150 |
| 7-guanidino-3-(2-phenylethoxy)-4-chloro-isocoumarin | 0.010 | 3900 |
| APMSF[b] | 0.125 | 230 |

[a]The inactivation rates were measured at 0.1 M Hepes, 0.5 M NaCl, pH 7.5, and 25° C., the reaction mixture contains 8% Me$_2$SO. Enzyme concentraton was 11–17 nM.
[b]The inhibition rate was measured at 0.1 M Hepes, 0.5 M NaCl, pH 7.0, 25° C.

TABLE IV

Inactivaton Rates for Inhibition of Serine Proteases by Substituted Isocoumarins[a]

| | $k_{obs}/[I]\ (M^{-1}s^{-1})$ | | | |
|---|---|---|---|---|
| Inhibitors | PPE[b] | HLE[c] | Chymotrysin[d] | Cathepsin G[e] |
| 3-(3-aminopropoxy)isocoumarin | 2.3 | 47 | 38 | 2.8 |
| 3-(3-aminopropoxy)-4-chloro-isocoumarin | 70 | 860 | 580 | 260 |
| 3-(2-isothiureidoethoxy)-4-chloro-isocoumarin | 270 | 220 | 1,300 | 110 |
| 3-(3-isothiureidopropoxy)-4-chloro-isocoumarin | 70 | 2,000 | 1,700 | 83 |
| 7-amino-3-(3-isothiureidopropoxy)-4-chloroisocoumarin | 1.0 | 630 | 4,400 | 36 |
| 7-guanidino-3-methoxyisocoumarin | 55 | 320 | 270 | —[f] |
| 7-guanidino-3-methoxy-4-chloro-isocoumarin | 860 | 6,400 | 7,200 | 11,000 |
| 7-guanidino-3-ethoxyisocoumarin | 86 | 1,900 | 990 | —[g] |
| 7-guanidino-3-ethoxy-4-chloro isocoumarin | 2,300 | 81,00 | 37,000 | 84,00 |
| 7-guanidino-3-(2-phenylethoxy)-isocoumarin | NI[h] | 0.9 | 2,600 | —[i] |
| 7-guanidino-3-(2-phenylethoxy)-4-chloriscoumarin | 5.7 | 73 | 38,000 | 66,000 |

[a]Inactivation rates were measured at 0.1 M Hepes, 0.5 NaCl, pH 7.5, 8–12% and 25° C. by incubation method. An aliquot of inhibitor was added to a solution of enzyme and aliquots removed with time and assayed for remaining activity.
[b]Inhibitor concentrations were from 0.01 to 0.51 mM.
[c]Inhibitor concentrations were from 0.001 to 0.18 mM.
[d]Inhibitor concentrations were from 0.004 to 0.33 mM.
[e]Inhibitor concentrations were from 0.002 to 0.35 mM.
[f]Inhibition was not time dependent, 81% inhibition was obtained at 0.49 mM.
[g]Inhibition was not time dependent, 87% inhibition was obtained at 47 μM.
[h]No inhibition.
[i]Inhibition was not time dependent, 87% inhibition was obtained at 0.53 mM.

TABLE V

Half-Lives for Spontaneous Hydrolysis of Isocoumarin Derivatives in Hepes Buffer[a] and in Human Plasma

| | $t_{\frac{1}{2}}$(min) | |
|---|---|---|
| Compounds | Hepes | Plasma |
| 3-(3-aminopropoxy)isocoumarin | 606 | |
| 3-(3-aminopropoxy)-4-chloroisocoumarin | 123 | |
| 3-(2-isothiureidoethoxy)-4-chloro isocoumarin | 83 | |
| 3-(3-isothiureidopropoxy)-4-chloro-isocoumarin | 99 | 0.5 |
| 7-amino-3-(3-isothiureidopropoxy) 4-chloroisocoumarin | 90 | 165 |
| 7-guanidino-3-methoxyisocoumarin | 252 | |
| 7-guanidino-3-methoxy-4-chloroisocoumarin | 44 | 6.7 |
| 7-guanidino-3-ethoxyisocoumarin | 136 | |
| 7-guanidino-3-ethoxy-4-chloroisocoumarin | 39 | 8.2 |
| 7-guanidino-3-(2-phenylethoxy)isocoumarin | 140 | |
| 7-guanidino-3-(2-phenylethoxy)-4-chloro-isocoumarin | 36 | 4.5 |

[a]Conditions were 0.1 Hepes, 0.5 M NaCl, pH 7.5 and 9% Me$_2$SO at 25° C. Spontaneous hydrolysis rates were measured spectrophotometrically by monitoring the decrease in absorbance due to the isocoumarin ring system (wavelength 335–380 nm) using the first-order rate law.

TABLE VI

The Prothrombin Time for Human Plasma in the Presence of Substituted Isocoumarin[a]

| | | prothrombin time (sec) | |
|---|---|---|---|
| Inhibitor | [I] (μM) | without preincubation | with preincubation |
| None | — | 11–14 | 11–14 |
| 3,4-dichloroisocoumarin | 330 | 120 | 14 |
| 7-guanidino-3-methoxy-4-chloroisocoumarin | 33 | 168 | 23 |
| 7-guanidino-3-ethoxy-4-chloroisocoumarin | 44 | >240 | 80 |
| 7-guanidino-3-(2-phenylethoxy)-4-chloroisocoumarin | 38 | 19 | 18 |
| 3-(3-isothiureidopropoxy)-4-chloroisocoumarin | 38 | 15 | 13 |
| 7-amino-3-(3-isothiureidopropoxy)-4-chloroisocoumarin | 31 | 14 | 15 |

[a]The prothrombin time described by Quick et. al., Am. J. Med. Sci. 190, pp 501–511 (1935) was used to measure the clotting time after adding calcium and tissue factor to the plasma or to the plasma with inhibitor.

The following examples are given to illustrate the invention and are not intended to limit it in any manner.

EXAMPLE 1

Preparation of 3-(2-Isothiureidoethoxy)-4-Chloroisocoumarin

2-Bromoethyl 2-carboxyphenylacetate was prepared from heating 10 g of homophthalic acid (56 mmole) and 21 g of 2-bromoethanol (167 mmole) in 175 ml of benzene with a few drops of conc. sulfuric acid at 90°–110° for two hours, yield 64%. TLC shows that it is a pure compound. The cyclization of 2-bromoethyl 2-carboxyphenylacetate with $PCl_5$ was performed by a previous method with modification (Tirodkar, and Usgaonkar, Indian. J. Chem. 7, pp 1114–1116 (1969)). 1.15 g of 2-bromoethyl 2-carboxyphenylacetate was heated with 2.1 g of $PCl_5$ in 90 ml of benzene at 70° C. for 2 hrs. The benzene was removed and the residue triturated with petroleum ether. The crude product was purified by silica gel column chromatography with methylene chloride as an eluent to give 560 mg of 3-(bromoethyl)-4-chloroisocoumarin (yield, 46%). IR and NMR spectra show it was the desired product. 100 mg of 3-bromomethyl-4-chloroisocoumarin (0.3 mmole) was heated with 60 mg of thiourea (0.8 mmole) in 5 ml of THF at 70° C. for 2 days to give a yellow solid, 50 mg (yield, 40%), m.p. 167°–169° C. (dec); one spot on TLC, $R_f=0.7$ (Butanol:acetic acid:water=6:1:5); NMR spectrum ($d_6$-DMSO), $\delta$ 9.1 (2b, 4H), 7.5–8.1 (m, 4H), 4.6 (t, 2H), 3.6 (t, 2H); mass spectrum (FAB+), m/e=299 (M+-Br). Anal. Calc. for $C_{12}H_{12}N_2O_3Br_1Cl_1S_1$: C, 37.96; H, 3.19; N, 7.38. Found: C, 37.81; H, 3.27; N, 7.71.

EXAMPLE 2

Preparation of 7-Guanidino-3-Methoxyisocoumarin

Methyl 2-carboxy-4-nitrophenyl acetate was prepared from 2-carboxy-4-nitrophenylacetate and methanol by the procedure described above. Hydrogenation of this nitro compound gives methyl 4-amino-2-carboxyphenylacetate (yield 90%). The guanidination of the amino compound with 3,5-dimethylpyrazole-1-carboxamidine nitrate (ADMP) was performed by a standard method described previously (Tsunematsu & Makismi, J. Biochem. 88, pp 1773–1783, (1980)). 2.2 g of amino compound (10 mmole), 1.9 g of triethylamine (19 mmole) and 3.0 g of ADMP (15 mmole) was heated in 20 ml of THF and refluxed for 18 hrs. The white precipitate was filtered and washed with cold methanol to give 1.5 g of methyl 2-carboxy-4-guanidinophenylacetate, (yield 46%). One spot on TLC, $R_f=0.6$ (Butanol:acetic acid:pyridine:water=4:1:1:2), it shows an orange color when sprayed with Sakaguchi reagent. NMR spectrum ($CF_3COOH$), $\delta$ 8.4, 7.7 (b, 4H), 6.6 (b, 4H) 4.4 (s, 2H), 4.1 (s, 3H). Anal. Calc. for $C_{11}H_{13}N_3O_4.\frac{1}{2}H_2O$: C, 50.77; H, 5.42; N, 16.15. Found: C, 51.03; H, 5.38; N, 16.19. 0.9 g of methyl 2-carboxy-4-guanidinophenylacetate (3 mmole) was heated with 1.5 g of $PCl_5$ (7.2 mmole) at 70°–80° C. for 2 hrs, white solid precipitated out during the heating. The solid was filtered off and purified by silica gel column chromatography with methylene chloride and methanol (5:1) as an eluent to give 0.5 g of 7-guanidino-3-methoxyisocoumarin (yield 59%). One spot on TLC, $R_f=0.7$ (Butanol:acetic acid:pyridine:water=4:1:1:2); m.p. 185°–186° C. (dec);, NMR spectrum ($d_6$-DMSO): $\delta$ 7.9, 7.6 (b, 3H), 7.7 (b, 4H), 6.1 (s, 1H), 3.9 (s, 3H); mass spectrum (FAB+), m/e=234 (M+-Cl). Anal. Calc. for $C_{11}H_{12}N_3O_3Cl_1.\frac{1}{2}H_2O$: C, 47.40; H, 4.67; N, 15.08; Cl, 12.75. Found: C, 47.42; H, 4.74; N, 15.05; Cl, 12.68.

EXAMPLE 3

Preparation of 7-Guanidino-3-Methoxy-4-Chloroisocoumarin 0.27 g of 7-guanidino-3-methoxyisocoumarin (1 mmole) was chlorinated with 0.15 g of N-chlorosuccinimide (1.1 mmole) in 5 ml DMF at r.t. overnight. The reaction mixture was evaporated to dryness, and purified by silica gel column chromatography which is eluted with methylene chloride and methanol (5:1) to give 0.1 g of 7-guanidino-3-methoxy-4-chloroisocoumarin (yield 34%). One spot on TLC, $R_f=0.75$ (Butanol:acetic acid:pyridine:water=4:1:1:2); NMR spectrum is similar to 7-guanidino-3-methoxyisocoumarin except no peak at 6.1 ppm; mass spectrum (FAB+), m/e=268 (M+-Cl). Anal. Calc. for $C_{11}H_{11}N_3O_3Cl_2.\frac{1}{2}H_2O$: C, 42.17; H, 3.83; N, 13.41; Cl, 22.68. Found: C, 42.65; H, 3.72; N, 13,28; Cl, 22.32.

EXAMPLE 4

Preparation of 3-(3-Aminopropoxy)isocoumarin Hydrochloride

Homophthalic acid (18 g, 0.1 mole) and 3-(benzyloxycarbonylamino)-1-propanol (41 g, 0.2 mole) were heated in 150 ml of benzene at 120°–130° C. for 2 hrs in the presence of a few drops of conc. $H_2SO_4$. Benzene was evaporated, and 200 ml of ethylacetate was added. The organic solution was washed with 4% $NaHCO_3$ twice (150 ml×2). The aqueous layer which contained the monoester salt was acidified with 5N HCl and extracted with ethylacetate. 33 g of 3-(benzyloxycarbonylamino)propyl 2-carboxyphenylacetate (yield, 89%) was obtained after the solvent was evaporated. Hydrogenation of this monoester (1.86 g, 5 mmole) was performed in methanol containing 0.3 ml of acetic acid and 10% palladium on carbon to give 1 g of 3-aminopropyl 2-carboxphenylacetate.HAc (yield, 67%). This compound was identified by its NMR spectrum and TLC (Butanol:acetic acid:pyridine:water=4:1:1:2). 2 g of 3-aminopropyl 2-carboxyphenylacetate.HAc (3 mmole) was heated with 1.6 g of $PCl_5$ (7.5 mmole) in 50 ml of anhydrous THF at 70°–80° for 2 hrs, a white precipitate formed. This white solid was purified by column chromatography (methylene chloride:methanol=5:1) and crystalline from MeOH-ether to give 0.2 g of 3-(3-aminopropoxy)isocoumarin.HCl (yield, 26%), m.p. 173°–174° C.; mass spectrum, m/e=220 (M+-Cl). Anal. Calc. for $C_{12}H_{14}N_1O_3Cl_1$: C, 56.37; H, 5.52; N, 5.48; Cl, 13.87. Found: C, 56.15; H, 5.49; N, 5.44; Cl 13.95.

EXAMPLE 5

Preparation of 3-(3-Aminopropoxy)-4-Chloroisocoumarin Hydrochloride 0.13 g of 3-(3-aminoproxy)isocoumarin hydrochloride (0.5 mmole) was chlorinated with 0.07 g of N-chlorosuccinimide (0.5 mmole) in 5 ml of DMF at r.t. overnight. The reaction mixture was purified by silica gel column chromatography (methylene chloride:methanol=5:1) and crystallized from MeOH-ether to give 0.09 g of 3-(3-aminopropoxy)-4-chloro-isocoumarin hydrochloride (yield, 60%). NMR spectrum of this compound is similar to 3-(3-aminopropoxy)isocoumarin without the peak at $\delta$ 6.2 ppm; m.p. 160°–163° C.; mass spectrum, m/e=254 (M+-Cl). Anal. Calc. for $C_{12}H_{13}N_1O_3Cl_2 \cdot \frac{1}{4}H_2O$: C, 48.88; H, 4.61; N, 4.75; Cl, 24.06. Found: C, 48.85; H, 4.54; N, 4.74; Cl, 24.02.

EXAMPLE 6

Preparation of 7-Amino-4-Chloro-3-(3-Isothiureidopropoxy)isocoumarin

This compound was synthesized by the same procedure as 3-(3-isothiureidopropoxy)-4-chloroisocoumarin. 3-Bromopropyl 2-carboxy-4-nitrophenylacetate was prepared from 2-carboxy-4-nitrophenylacetate and 3-bromopropanol, yield 60%. Cyclization of the monoester with $PCl_5$ gives 3-bromopropoxy-4-chloro-7-nitroisocoumarin (yield, 60%). Hyrogenation of the nitro compound (0.36 g) in methanol gives 0.12 g of 7-amino-3-bromopropoxy-4-chloroisocoumarin, which is purified by silica gel column chromatography with methylene chloride as an eluent (yield, 36%). This aminoisocoumarin reacts with thiourea in THF to give the final product, which can be crystallized from MeOH-ether (yield, 40%), mp 160°–162° C. (dec); one spot on TLC, $R_f=0.6$ (Butanol:acetic acid:pyridine water=4:1:1:2); mass spectrum (FAB+), m/e=328 (M+-Br). Anal. Calc. for $C_{13}H_{15}N_3O_3Cl_1Br_1S_1$: C, 38.20; H, 3.70; N, 10.28; Cl, 8.67. Found: C, 38.15; H, 3.73; N, 10.25; Cl, 8.63.

What is claimed is:

1. A compound of the formula:

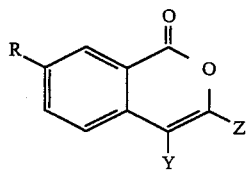

or a pharmaceutically acceptable salt thereof, wherein
R is selected from the group consisting of —NH—C(=NH)—NH₂, —C(=NH)NH₂, amino-$C_{1-6}$ alkyl, and isothiureido-$C_{1-6}$ alkyl,
Z is selected from the group consisting of H, halogen, $C_{1-6}$ alkyl, $C_{1-6}$ alkyl with a phenyl group attached to the alkyl group, $C_{1-6}$ fluorinated alkyl, $C_{1-6}$ alkyl with an hydroxyl group attached to the alkyl group, $C_{1-6}$ alkyl with a $C_{1-6}$ alkoxy group attached to the alkyl group, $C_{1-6}$ alkoxy, $C_{1-6}$ fluorinated alkoxy, $C_{1-6}$ alkoxy with a phenyl group attached to the alkoxy group, benzyloxy group wherein the phenyl group is unsubstituted or substituted by one or two substituents selected from halogen, trifluoromethyl, $NO_2$, cyano, methyl, methoxy, acetyl, carbonyl, OH, and amino, and
Y is selected from the group consisting of H, halogen, trifluoromethyl, methyl, OH, and methoxy.

2. A compound of the formula:

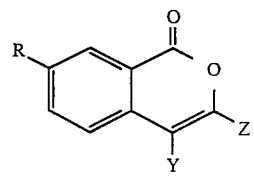

or a pharmaceutically acceptable salt thereof, wherein
Z is selected from the group consisting of $C_{1-6}$ alkoxy with an amino group attached to the alkoxy group, $C_{1-6}$ alkoxy with an isothiureido group attached to the alkoxy group, $C_{1-6}$ alkoxy with a guanidino group attached to the alkoxy group, $C_{1-6}$ alkoxy with an amidino group attached to the alkoxy group, $C_{1-6}$ alkyl with an amino group attached to the alkyl group, $C_{1-6}$ alkyl with an isothiureido group attached to the alkyl group, $C_{1-6}$ alkyl with a guanidino group attached to the alkyl group, $C_{1-6}$ alkyl with an amidino group attached to the alkyl group,
R is selected from the group consisting of H, OH, $NH_2$, $NO_2$, halogen, $C_{1-6}$ alkoxy, $C_{1-6}$ fluorinated alkoxy, $C_{1-6}$ alkyl, amino-$C_{1-6}$ alkyl, and
Y is selected from the group consisting of H, halogen, trifluoromethyl, methyl, OH and methoxy.

3. A compound of the formula:

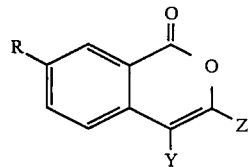

or a pharmaceutically acceptable salt thereof, wherein
R is selected from the group consisting of —NH—C(=NH)—NH₂, —C(=NH)NH₂, amino-$C_{1-6}$ alkyl, and isothiureido-$C_{1-6}$ alkyl,
Z is selected from the group consisting of $C_{1-6}$ alkoxy with an amino group attached to the alkoxy group, $C_{1-6}$ alkoxy with an isothiureido group attached to the alkoxy group, $C_{1-6}$ alkoxy with a guanidino group attached to the alkoxy group, $C_{1-6}$ alkoxy with an amidino group attached to the alkoxy group, $C_{1-6}$ alkyl with an amino group attached to the alkyl group, $C_{1-6}$ alkyl with an isothiureido group attached to the alkyl group, $C_{1-6}$ alkyl with a guanidino group attached to the alkyl group, $C_{1-6}$ alkyl with an amidino group attached to the alkyl group, and
Y is selected from the group consisting of H, halogen, trifluoromethyl, methyl, OH and methoxy.

* * * * *